United States Patent
Park et al.

(10) Patent No.: US 8,742,410 B2
(45) Date of Patent: Jun. 3, 2014

(54) FUSED POLYCYCLIC HETEROAROMATIC COMPOUND, ORGANIC THIN FILM INCLUDING THE COMPOUND AND ELECTRONIC DEVICE INCLUDING THE ORGANIC THIN FILM

(71) Applicant: Samsung Electronics Co., Ltd., Suwon-si (KR)

(72) Inventors: Jeong Il Park, Seongnam-si (KR); Jong Won Chung, Hwaseong-si (KR); Bang Lin Lee, Suwon-si (KR); Ji Young Jung, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/866,290

(22) Filed: Apr. 19, 2013

(65) Prior Publication Data
US 2013/0277657 A1    Oct. 24, 2013

(30) Foreign Application Priority Data

Apr. 20, 2012  (KR) .................. 10-2012-0041653

(51) Int. Cl.
*H01L 51/00* (2006.01)
(52) U.S. Cl.
USPC .............. 257/40; 438/99; 257/E51.022
(58) Field of Classification Search
USPC .............. 257/40, 642, E25.008, E51.003, 257/E51.022; 438/82, 99
See application file for complete search history.

(56) References Cited

U.S. PATENT DOCUMENTS

| | | | |
|---|---|---|---|
| 5,946,551 A | 8/1999 | Dimitrakopoulos et al. | |
| 6,232,157 B1 | 5/2001 | Dodabalapur et al. | |
| 7,816,673 B2 | 10/2010 | Park et al. | |
| 8,124,964 B2 * | 2/2012 | Takimiya et al. | 257/40 |

FOREIGN PATENT DOCUMENTS

WO    WO-2009/009790 A1    1/2009

OTHER PUBLICATIONS

Anatoliy N. Sokolov, Sule Atahan-Evrenk, Rajib Mondal, Hylke B. Akkerman, Roel S. Sanchez-Carrera, Sergio Granados-Focil, Joshua Schrier, Stefan C. B. Mannsfeld, Arjan P. Zoombelt, Zhenan Bao, Alan Aspuru-Guzik, Nature Commun. 2011, 2, 437 (DOI:10.1038/ncomms1451).

* cited by examiner

*Primary Examiner* — Quoc Hoang
(74) *Attorney, Agent, or Firm* — Harness, Dickey & Pierce, P.L.C.

(57) ABSTRACT

A low-molecular-weight fused polycyclic heteroaromatic compound, an organic thin film and an electronic device including the fused polycyclic heteroaromatic compound, include a compact planar structure in which six or more rings are fused together, and thereby exhibits high charge mobility, and furthermore, enables the use of a deposition process or a room-temperature solution process when applied to devices, therefore realizing improved processibility.

14 Claims, 1 Drawing Sheet

FUSED POLYCYCLIC HETEROAROMATIC COMPOUND, ORGANIC THIN FILM INCLUDING THE COMPOUND AND ELECTRONIC DEVICE INCLUDING THE ORGANIC THIN FILM

CROSS-REFERENCE TO RELATED APPLICATION

This application claims the benefit of priority under 35 U.S.C. §119 to Korean Patent Application No. 10-2012-0041653 filed in the Korean Intellectual Property Office (KIPO) on Apr. 20, 2012, the entire contents of which are incorporated herein by reference.

BACKGROUND

1. Field

Example embodiments relate to a fused polycyclic heteroaromatic compound, an organic thin film including the same, and an electronic device including the organic thin film.

2. Description of the Related Art

In general, flat display devices (e.g., liquid crystal displays or organic electroluminescent displays) are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, as a material for a channel of the TFT, organic materials (e.g., pentacene or polythiophene) have been studied. In the case of polymer or oligomer organic materials, e.g., F8T2 (poly(9,9-dioctylfluorene-co-bithiophene)) as polythiophene-based materials, a solution process (e.g., spin casting), may be desirably applied. However, problems of decreased charge mobility and increased off-state leakage current may be caused. Further, low-molecular-weight organic materials (e.g., pentacene) may have high charge mobility of about 3.2 to about 5.0 cm$^2$/Vs or more, but may require a relatively expensive apparatus for vacuum deposition at the time of forming a thin film. Therefore, the low-molecular-weight organic material may be unsuitable for use in the preparation of a film having a relatively large area, and processibility may be undesirable.

Thus, there have been attempts to devise materials for channel layers having increased charge mobility and improved processibility. The related art discloses dimeric bisbenzodithiophene, in which rings may be fused in groups of three and thus increased charge mobility may be realized.

However, the development of an organic semiconductor material, satisfying improved electrical properties and processibility, may still be required in the art.

SUMMARY

Example embodiments relate to a fused polycyclic heteroaromatic compound, an organic thin film including the same, and an electronic device including the organic thin film.

Example embodiments provide a low-molecular-weight fused polycyclic heteroaromatic compound that has a compact planar structure in which six or more rings are fused together, and thereby exhibits high charge mobility, and furthermore, enables the use of a deposition process or a room-temperature solution process when applied to devices, therefore realizing improved processibility.

Other example embodiments provide an organic thin film including the fused polycyclic heteroaromatic compound.

Yet other example embodiments provide an electronic device including the organic thin film as a carrier transport layer.

According example embodiments, a fused polycyclic heteroaromatic compound represented by the following Chemical Formula 1 is provided.

[Chemical Formula 1]

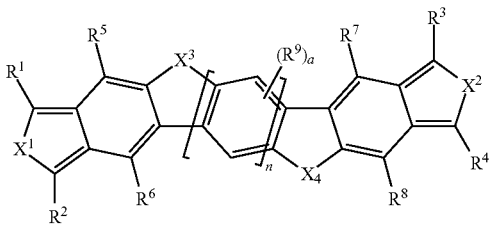

In Chemical Formula 1, $X^1$ and $X^2$ are each independently O, S, Se, Te, or N—$R^a$, wherein $R^a$ is hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group (—OR$^{11}$, wherein R$^{11}$ is a substituted or unsubstituted C6 to C30 aryl group), a substituted or unsubstituted C4 to C30 cycloalkyl group, a substituted or unsubstituted C4 to C30 cycloalkyloxy group (—OR$^{12}$, wherein R$^{12}$ is a substituted or unsubstituted C4 to C30 cycloalkyl group), a substituted or unsubstituted C2 to C30 heteroaryl group, an acyl group (—C(=O)R$^{13}$, wherein R$^{13}$ is a substituted or unsubstituted $C_1$ to $C_{30}$ alkyl group), a sulfonyl group (—S(=O)R$^{14}$, wherein R$^{14}$ is a substituted or unsubstituted C1 to C30 alkyl group), or a carbamate group (—NH$_2$C(=O) OR$^{15}$, wherein R$^{15}$ is a substituted or unsubstituted C1 to C30 alkyl group), $X^3$ and $X^4$ are each independently O, S, Se, Te, N—$R^b$, or CR$^c$R$^d$ wherein R$^b$ to R$^d$ are each independently hydrogen, a substituted or unsubstituted linear or branched C1 to C30 alkyl group, a substituted or unsubstituted $C_7$ to $C_{30}$ arylalkyl group, a substituted or unsubstituted C6 to C30 aryl group, a substituted or unsubstituted C1 to C30 alkoxy group, a substituted or unsubstituted C6 to C30 aryloxy group (—OR$^{11}$, wherein R$^{11}$ is a substituted or unsubstituted C6 to C30 aryl group), a substituted or unsubstituted C4 to C30 cycloalkyl group, a substituted or unsubstituted C4 to C30 cycloalkyloxy group (—OR$^{12}$, wherein R$^{12}$ is a substituted or unsubstituted C4 to C30 cycloalkyl group), a substituted or unsubstituted C2 to C30 heteroaryl group, an acyl group (—C(=O)R$^{13}$, wherein R$^{13}$ is a substituted or unsubstituted C1 to C30 alkyl group), a sulfonyl group (—S(=O)R$^{14}$, wherein R$^{14}$ is a substituted or unsubstituted C1 to C30 alkyl group), or a carbamate group (—NH$_2$C(=O)OR$^{15}$, wherein R$^{15}$ is a substituted or unsubstituted C1 to C30 alkyl group), $R^1$, $R^2$, $R^3$, $R^4$, $R^5$, $R^6$, $R^7$, $R^8$, and $R^9$ are each independently hydrogen, a halogen (—F, —Cl, —Br, or —I), a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group, n is an integer ranging from 0 to 3, and a is an integer of 1 or 2.

The fused polycyclic heteroaromatic compound may be a fused polycyclic heteroaromatic compound represented by the following Chemical Formulae 1A to 1F.

[Chemical Formula 1A]

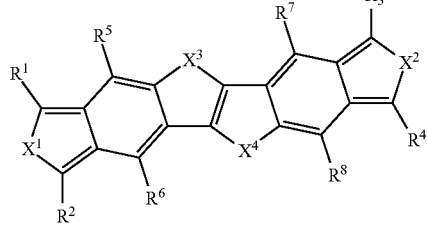

[Chemical Formula 1B]

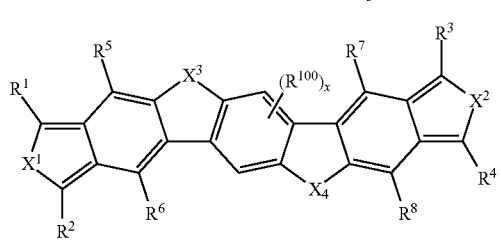

[Chemical Formula 1C]

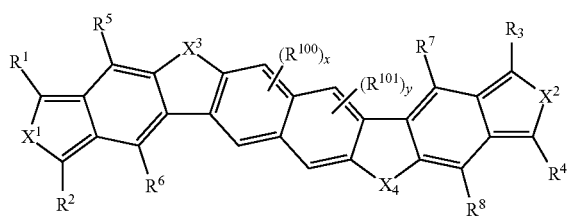

[Chemical Formula 1D]

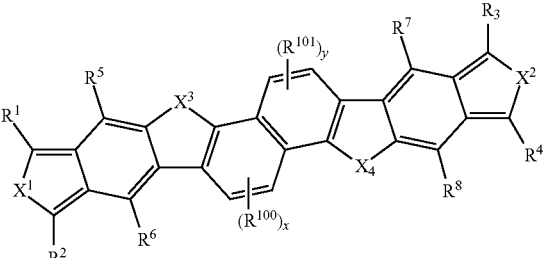

[Chemical Formula 1E]

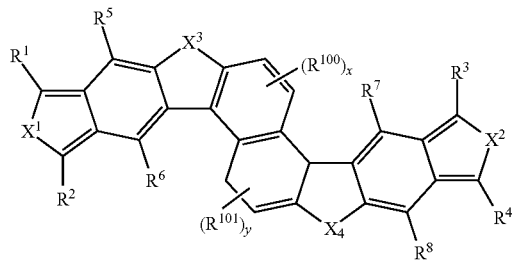

[Chemical Formula 1F]

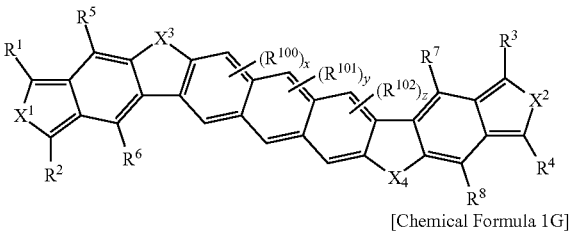

[Chemical Formula 1G]

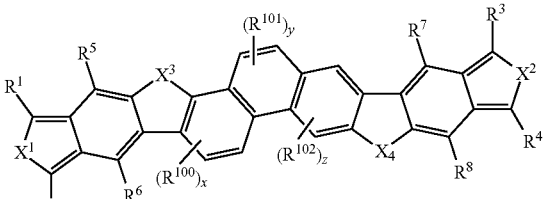

[Chemical Formula 1H]

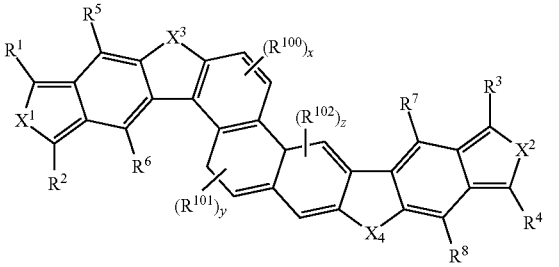

In Chemical Formulae 1A to 1H, $X^1$, $X^2$, $X^3$, $X^4$, $R^1$, $R^2$, $R^3$, $R^4$, $R^5$, $R^6$, $R^7$, and $R^8$ are the same as in Chemical Formula 1, $R^{100}$ to $R^{102}$ are each independently the same as $R^9$ of Chemical Formula 1, and x, y, and z is an integer of 1 or 2.

In Chemical Formula 1, $X^1$, $X^2$, $X^3$, and $X^4$ are sulfur (S).

The fused polycyclic heteroaromatic compound may have an average molecular weight of about 350 to about 3000.

In Chemical Formula 1, n may be an integer ranging from 1 to 3.

In Chemical Formula 1, at least one of $X^1$, $X^2$, $X^3$, and $X^4$ may be sulfur (S).

In Chemical Formula 1, at least one of $R^1$, $R^2$, $R^3$, $R^4$, $R^5$, $R^6$, $R^7$, $R^8$, and $R^9$ may be independently a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30. heteroaryl group.

According to other example embodiments, an organic thin film and an electronic device including the fused polycyclic heteroaromatic compound are provided.

The electronic device may include a transistor having an active layer formed of the fused polycyclic heteroaromatic compound in a channel region.

BRIEF DESCRIPTION OF THE DRAWINGS

Example embodiments will be more clearly understood from the following detailed description taken in conjunction with the accompanying drawings.

FIG. 1 is a schematic cross-sectional view of a transistor according to example embodiments.

FIG. 2 is a schematic cross-sectional view of a transistor according to other example embodiments.

DETAILED DESCRIPTION

Figure 1:
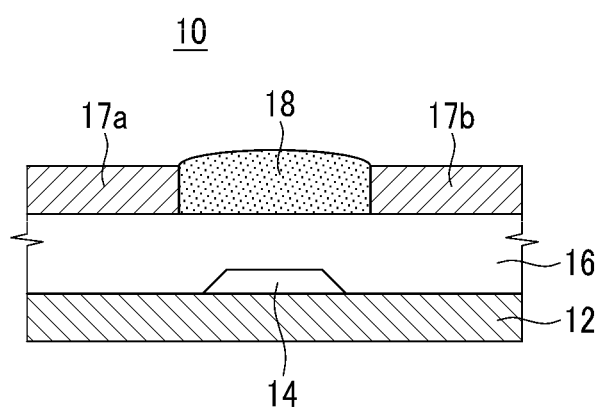
FIGS. 1 and 2 represent non-limiting, example embodiments as described herein.

Various example embodiments will now be described more fully with reference to the accompanying drawings in which some example embodiments are shown. However, specific structural and functional details disclosed herein are merely representative for purposes of describing example embodiments, and thus may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope of the disclosure.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

As used herein, the term "combination thereof" refers to a mixture, a stacked structure, a composite, an alloy, or the like.

As used herein, when a definition is not otherwise provided, the term "hetero" may refer to one including 1 to 4 heteroatoms selected from N, O, S, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. The term "heterocycloalkyl group" may be at least one non-aromatic ring including a heteroatom, and the term "heteroaryl group" may be at least one aromatic ring including a heteroatom. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an isoamyl group, a hexyl group, and the like).

The term "alkenyl group" may refer to a linear or branched saturated monovalent hydrocarbon group including at least one carbon-carbon double bond (e.g., an ethenyl group).

The term "alkynyl group" may refer to a linear or branched saturated monovalent hydrocarbon group including at least one carbon-carbon (e.g., ethynyl group).

The term "alkoxy group" may refer to an alkyl group that is linked via an oxygen (e.g., a methoxy, an ethoxy, and a sec-butyloxy group).

The term "aryl group" may refer to a monovalent functional group formed by the removal of one hydrogen atom from one or more rings of an arene (e.g., phenyl or naphthyl). The arene may refer to a hydrocarbon having an aromatic ring, and includes monocyclic and polycyclic hydrocarbons wherein the additional ring(s) of the polycyclic hydrocarbon may be aromatic or nonaromatic.

The term "aryloxy group" may refer to an aryl group that is linked via an oxygen, and the aryl group is the same as described above.

The "arylalkyl group" may refer to an aryl group where at least one hydrogen is substituted with a lower alkylene (e.g., methylene, ethylene, propylene, and the like). For example, the "arylalkyl group" may be a benzyl group or a phenylethyl group.

The term "cycloalkyl group" may refer to a monovalent functional group having one or more saturated rings in which all ring members are carbon (e.g., a cyclopentyl group and a cyclohexyl) group.

The term "cycloalkenyl group" may refer to a monovalent functional group including at least one ring having a carbon-carbon double bond, wherein all ring members are carbon (e.g., a cyclopentenyl group or a cyclohexenyl group).

The term "cycloalkynyl group" may refer to an aliphatic monocyclic and polycyclic functional group including at least one carbon-carbon triple bond.

The term "heteroarylalkyl group" may refer to an alkyl group where at least one hydrogen is substituted with a heteroaryl group.

The term "alkylheteroaryl group" may refer to a heteroaryl group where at least one hydrogen is substituted with an alkyl group.

As used herein, when a definition is not otherwise provided, "aromatic ring" refers to a functional group in which all atoms in the cyclic functional group have a p-orbital, wherein these p-orbitals are conjugated. For example, the aromatic ring may be a C6 to C20 aryl group.

As used herein, when a definition is not otherwise provided, "heteroaromatic ring" refers to a functional group including a heteroatom selected from N, O, and S in a ring in which all atoms in the cyclic functional group have a p-orbital, wherein the p-orbital is conjugated. For example, the heteroaromatic ring may be a C3 to C20 heteroaryl group.

As used herein, when a definition is not otherwise provided, the term "alicyclic ring" may refer to non-conjugated ring, for example a C3 to C20 cycloalkyl group, a C3 to C20 heterocycloalkyl group, a C3 to C20 cycloalkenyl group, a C3 to C20 heterocycloalkenyl group, and the like.

As used herein, when a definition is not otherwise provided, the term "substituted" means that a compound or group is substituted with at least one substituent selected independently from a halogen (—F, —Cl, —Br, or —I), a C1 to C30 linear or branched alkyl group, for example a C1 to C10 linear or branched alkyl group, C2 to C30 linear or branched alkenyl group, for example a C2 to C10 linear or branched alkenyl group, a C2 to C30 linear or branched alkynyl group, for example a C2 to C10 linear or branched alkynyl group, a C6 to C30 aryl group, for example a C6 to C12 aryl group, a C2 to C30 heteroaryl group, for example a C2 to C12 heteroaryl group, a C3 to C30 cycloalkyl group, a C1 to C20 fluoroalkyl group, a C1 to C20 perfluoroalkyl group ($C_nF_{2n+1}$), a C1 to C30 linear or branched alkoxy group, a C3 to C30 cycloalkoxy group, a C2 to C30 linear or branched alkoxyalkyl group, a C4 to C30 cycloalkoxyalkyl group, a cyano group, an amino group (—NRR', wherein R and R' are independently hydrogen or a C1 to C10 alkyl group), an amidino group (—C(=NH)NH$_2$), a nitro group (—NO$_2$), an amide group (—C(=O)N(H)R, wherein R is hydrogen or a C1 to C10 alkyl group), an aldehyde group (—C(=O)H), a hydroxyl group (—OH), a sulfonyl group (—S(=O)$_2$R, wherein R is independently hydrogen or a C1 to C10 alkyl group), and a carbamate group (—NH$_2$C(=O)OR, wherein R is a C1 to C10 alkyl group) instead of hydrogen, provided that the substituted atom's normal valence is not exceeded.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments relate to a fused polycyclic heteroaromatic compound, an organic thin film including the same, and an electronic device including the organic thin film.

According to example embodiments, a fused polycyclic heteroaromatic compound having a compact planar structure in which six or more rings may be fused together the following Chemical Formula 1 is provided.

[Chemical Formula 1]

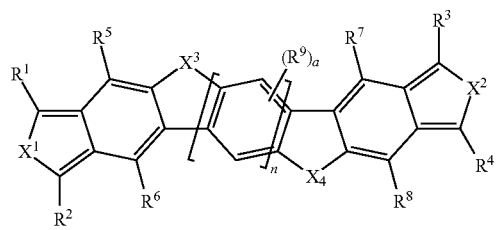

In Chemical Formula 1, $X^1$ and $X^2$ are each independently O, S, Se, Te, or N—$R^a$, wherein $R^a$ is hydrogen, a substituted or unsubstituted linear or branched C1 to C30 alkyl group, for example a substituted or unsubstituted linear or branched C1 to C20 alkyl group, a substituted or unsubstituted C7 to C30 arylalkyl group, for example a substituted or unsubstituted C7 to C20 arylalkyl group, a substituted or unsubstituted C6 to C30 aryl group, for example a substituted or unsubstituted C6 to C20 aryl group, a substituted or unsubstituted C1 to C30 alkoxy group, for example a substituted or unsubstituted C1 to C20 alkoxy group, a substituted or unsubstituted C6 to C30 aryloxy group, for example a substituted or unsubstituted C6 to C20 aryloxy group (—$OR^{11}$, wherein $R^{11}$ is a substituted or unsubstituted C6 to C30 aryl group, for example C6 to C20 aryl group), a substituted or unsubstituted C4 to C30 cycloalkyl group, for example a substituted or unsubstituted C4 to C20 cycloalkyl group, a substituted or unsubstituted C4 to C30 cycloalkyloxy group, for example a substituted or unsubstituted C4 to C20 cycloalkyloxy group (—$OR^{12}$, wherein $R^{12}$ is a substituted or unsubstituted C4 to C30 cycloalkyl group, for example a substituted or unsubstituted C4 to C20 cycloalkyl group), a substituted or unsubstituted C2 to C30 heteroaryl group, for example a substituted or unsubstituted C2 to C20 heteroaryl group, an acyl group (—C(=O)$R^{13}$, wherein $R^{13}$ is a substituted or unsubstituted C1 to C30 alkyl group, for example C1 to C20 alkyl group), a sulfonyl group (—S(=O)$R^{14}$, wherein $R^{14}$ is a substituted or unsubstituted C1 to C30 alkyl group, for example C1 to C20 alkyl group), or a carbamate group (—NH$_2$C(=O)$OR^{15}$, wherein $R^{15}$ is a substituted or unsubstituted C1 to C30 alkyl group, for example C1 to C20 alkyl group), $X^3$ and $X^4$ are each independently O, S, Se, Te, N, N—$R^b$, or C$R^cR^d$, wherein $R^b$ to $R^d$ are each independently hydrogen, a substituted or unsubstituted linear or branched C1 to C30 alkyl group, for example a substituted or unsubstituted linear or branched C1 to C20 alkyl group, a substituted or unsubstituted C7 to C30 arylalkyl group, for example a substituted or unsubstituted C7 to C20 arylalkyl group, a substituted or unsubstituted C6 to C30 aryl group, for example a substituted or unsubstituted C6 to C20 aryl group, a substituted or unsubstituted C1 to C30 alkoxy group, for example a substituted or unsubstituted C1 to C20 alkoxy group, a substituted or unsubstituted C6 to C30 aryloxy group, for example a substituted or unsubstituted C6 to C20 aryloxy group (—$OR^{11}$, wherein $R^{11}$ is a substituted or unsubstituted C6 to C30 aryl group, for example C6 to C20 aryl group), a substituted or unsubstituted C4 to C30 cycloalkyl group, for example a substituted or unsubstituted C4 to C20 cycloalkyl group, a substituted or unsubstituted C4 to C30 cycloalkyloxy group, for example a substituted or unsubstituted C4 to C20 cycloalkyloxy group (—$OR^{12}$, wherein $R^{12}$ is a substituted or unsubstituted C4 to C30 cycloalkyl group, for example a substituted or unsubstituted C4 to C20 cycloalkyl group), a substituted or unsubstituted C2 to C30 heteroaryl group, for example a substituted or unsubstituted C2 to C20 heteroaryl group, an acyl group (—$C(=O)R^{13}$, wherein $R^{13}$ is a substituted or unsubstituted C1 to C30 alkyl group, for example C1 to C20 alkyl group), a sulfonyl group (—$S(=O)R^{14}$, wherein $R^{14}$ is a substituted or unsubstituted C1 to C30 alkyl group, for example C1 to C20 alkyl group), or a carbamate group (—$NH_2C(=O)OR^{15}$, wherein $R^{15}$ is a substituted or unsubstituted C1 to C30 alkyl group, for example C1 to C20 alkyl group), provided both $X^3$ and $X^4$ are not $CR^b$, $R^1$, $R^2$, $R^3$, $R^4$, $R^5$, $R^6$, $R^7$, $R^8$ and $R^9$ are each independently hydrogen, halogen, a substituted or unsubstituted linear or branched C1 to C30 alkyl group, a substituted or unsubstituted linear or branched C2 to C30 alkenyl group, a substituted or unsubstituted linear or branched C2 to C30 alkynyl group, for example a substituted or unsubstituted linear or branched C2 to C20 alkynyl group, a substituted or unsubstituted C7 to C30 arylalkyl group, for example a substituted or unsubstituted C7 to C20 arylalkyl group, a substituted or unsubstituted C2 to C30 heteroarylalkyl group, for example a substituted or unsubstituted C2 to C20 heteroarylalkyl group, a substituted or unsubstituted C2 to C30 alkylheteroaryl group, for example a substituted or unsubstituted C2 to C20 alkylheteroaryl group, a substituted or unsubstituted C5 to C30 cycloalkyl group, for example a substituted or unsubstituted C5 to C20 cycloalkyl group, a substituted or unsubstituted C2 to C30 heterocycloalkyl group, for example a substituted or unsubstituted C2 to C20 heterocycloalkyl group, a substituted or unsubstituted C6 to C30 aryl group, for example a substituted or unsubstituted C6 to C20 aryl group, or a substituted or unsubstituted C2 to C30 heteroaryl group, for example a substituted or unsubstituted C2 to C20 heteroaryl group, n is an integer ranging from 0 to 3, and
a is an integer of 1 or 2.

The fused polycyclic heteroaromatic compounds represented by the above Chemical Formula 1 have a structure in which six or more aromatic rings and heteroaromatic rings are fused. By having a compact planar molecular structure, the fused polycyclic heteroaromatic compound has a uniform and stable oxidation potential when applied to an actual device and shows high charge mobility because the intermolecular packing and stacking are improved. Thereby, it is easily synthesized to be effectively applied to a semiconductor material, an electron transporting material, or the like. In other words, benzene rings are positioned in both Chemical Formula 1 in the center of thieno[3,2-b]thiophene or two thiophenes fused with an aromatic ring at both sides, and an $X^1$-containing hetero-ring and an $X^2$-containing hetero-ring are condensed in the benzene ring to enlarge the conjugation structure and to enhance the intermolecular interaction.

In addition, by positioning a hetero-ring between benzene rings, the solubility of the fused polycyclic heteroaromatic compound for the organic solvent may be improved. By introducing a C10 to C30 long aliphatic chain group (e.g., a substituted or unsubstituted C10 to C30 alkyl group or a substituted or unsubstituted C10 to C30 alkenyl group) into $R^1$, $R^2$, $R^3$, $R^4$, $R^5$, $R^6$, $R^7$, $R^8$, or $R^9$, solubility of the fused polycyclic heteroaromatic compound for the organic solvent may be improved. Due to the solubility improvement, it may be simply coated by a solution process at room temperature as well as in a deposition process, and the thin film may be formed in a wide area so the processibility and the workability are improved.

In Chemical Formula 1, because $X^1$ and $X^2$, and $X^3$ and $X^4$, are respectively positioned symmetrically to each other, the packing or stacking characteristics may be enhanced.

In the above Chemical Formula 1, $X^1$, $X^2$, $X^3$, and $X^4$ may be sulfur (S).

The fused polycyclic heteroaromatic compound may be represented by the following Chemical Formula 1A when n is 0 in Chemical Formula 1; may be represented by the following Chemical Formula 1B, when n is 1; may be represented by the following Chemical Formulae 1C to 1E, when n is 2; and may be represented by the following Chemical Formula 1F to 1H, when n is 3.

[Chemical Formula 1A]

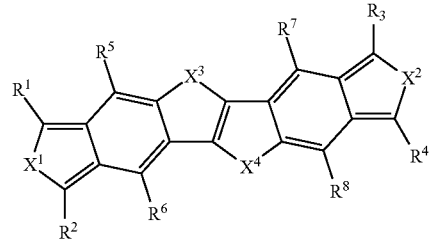

[Chemical Formula 1B]

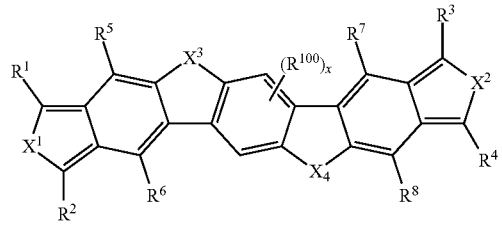

[Chemical Formula 1C]

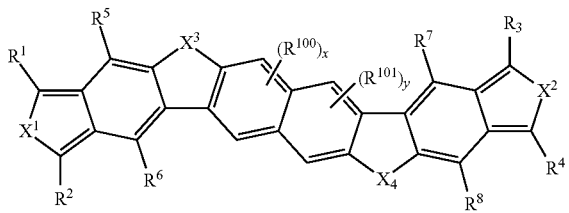

-continued

[Chemical Formula 1D]

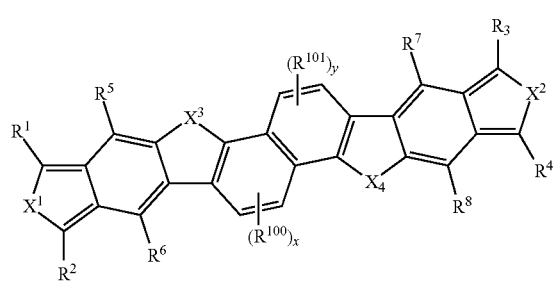

[Chemical Formula 1E]

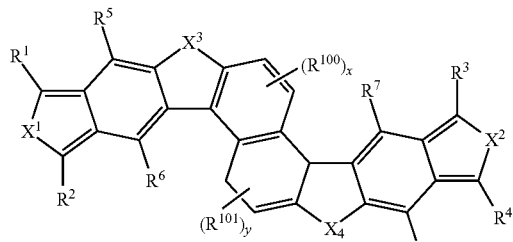

[Chemical Formula 1F]

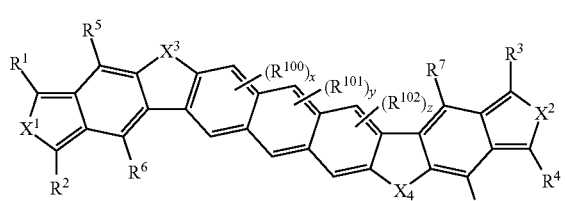

[Chemical Formula 1G]

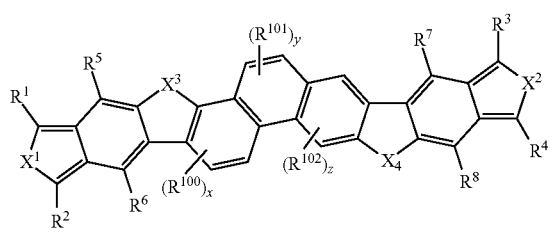

[Chemical Formula 1H]

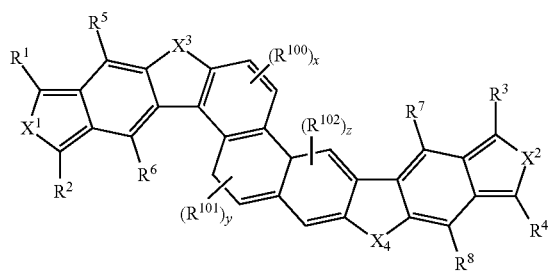

In Chemical Formulae 1A to 1H, $X^1$, $X^2$, $X^3$, $X^4$, $R^1$, $R^2$, $R^3$, $R^4$, $R^5$, $R^6$, $R^7$, and $R^8$ are the same as in Chemical Formula 1, $R^{100}$ to $R^{102}$ are each independently the same as $R^9$ of Chemical Formula 1, and x, y and z is an integer of 1 or 2.

In Chemical Formulae 1A to 1D, $X^1$ and $X^2$ may be sulfur (S), and $X^3$ and $X^4$ may be sulfur (S).

Examples of the fused polycyclic heteroaromatic compound may include the following compounds (1) to (8).

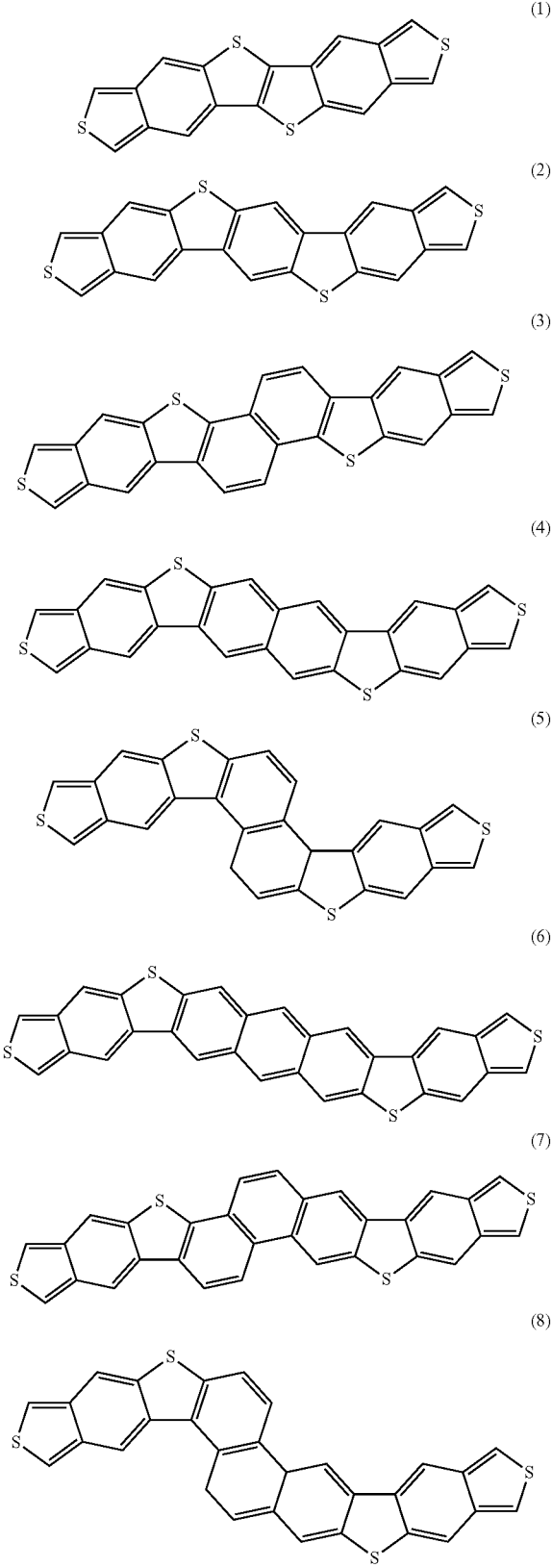

The reorganization energy of compounds (1) to (5) among the compounds (1) to (8) is calculated by using the Gaussian 03 program in DFT B3PW91 6-311G+ (d,p) level, and the results are shown in the following Table 1. For comparison, the reorganization energy of the following compounds ref-1 and ref-2 is also shown in Table 1.

TABLE 1 ref-1 ref-2

| Compound | $E_{HOMO}$ (eV) | $E_{LUMO}$ (eV) | Δ E (eV) | Reorganization Energy (eV) |
|---|---|---|---|---|
| compound ref-1 | −5.61 | −1.76 | 3.84 | 0.135 |
| compound ref-2 | −5.57 | −1.99 | 3.57 | 0.162 |
| compound 1 | −5.19 | −2.44 | 2.75 | 0.103 |
| compound 2 | −5.26 | −2.42 | 2.85 | 0.068 |
| compound 3 | −5.28 | −2.35 | 2.93 | 0.065 |
| compound 4 | −5.34 | −2.45 | 2.89 | 0.069 |
| compound 5 | −5.28 | −2.46 | 2.81 | 0.064 |

As shown in Table 1, the compounds (1) to (5) have lower reorganization energies than compounds ref-1 and ref-2. From the results, the compounds (1) to (5) have improved charge mobility compared to ref-1 and ref-2.

The fused polycyclic heteroaromatic compound according to example embodiments may be prepared according to a general method, for example, chemical or electrochemical oxidation synthesis, which is a representative method of polymerizing an aromatic compound or a heteroaromatic compound, or condensation polymerization using a compound of an organic transition element such as nickel or palladium.

For example, the compound represented by Chemical Formula 1 may be prepared through cyclization reaction of an intermediate compound represented by Chemical Formula 1-1. The cyclization reaction may be performed by the method described in, for example, J. Org. Chem. 2005, 70, 4502-4505.

[Chemical Formula 1-1]

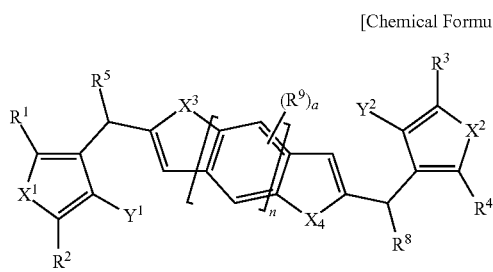

In Chemical Formula 1-1,
$X^1$, $X^2$, $X^3$, $X^4$, $R^1$, $R^2$, $R^3$, $R^4$, $R^5$, $R^6$, $R^7$, $R^8$, $R^9$, n, and a are the same as in Chemical Formula 1, $Y^1$ is a carbonyl group (—C(=O)$R^6$, wherein $R^6$ is the same as in Chemical Formula 1) or a halogen (e.g., —Br), $Y^2$ is a carbonyl group (—C(=O)$R^7$, wherein $R^7$ is the same as in Chemical Formula 1) or a halogen (e.g., —Br). For example, the fused polycyclic heteroaromatic compound where $X^1$, $X^2$, $X^3$, and $X^4$ are sulfur (S), $R^1$, $R^2$, $R^3$, $R^4$, $R^5$, $R^6$, $R^7$, and $R^8$ are hydrogen in Chemical Formula 1A may be synthesized according to the following Reaction Scheme 1, and the fused polycyclic heteroaromatic compound where $X^1$, $X^2$, $X^3$ and $X^4$ are sulfur (S), $R^1$, $R^2$, $R^3$, $R^4$, $R^5$, $R^6$, $R^7$, $R^8$, and $R^{100}$ are hydrogen may be synthesized according to the following Reaction Scheme 2, but they may be synthesized without limitation.

[Reaction Scheme 1]

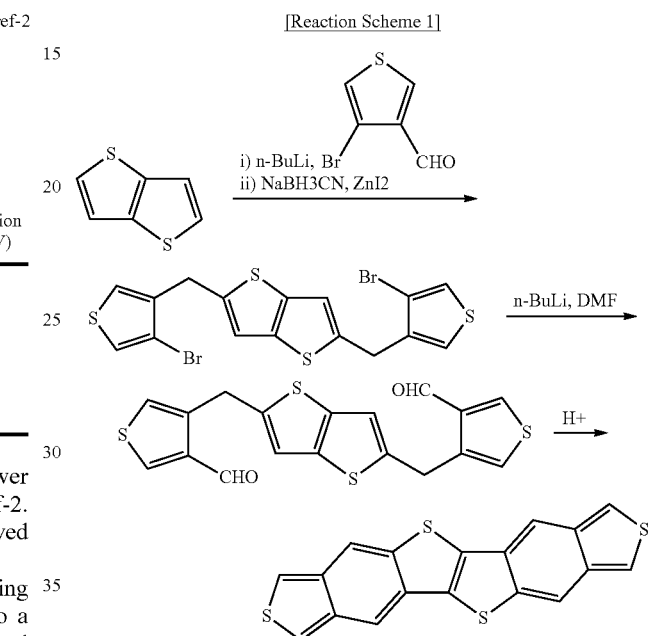

[Reaction Scheme 2]

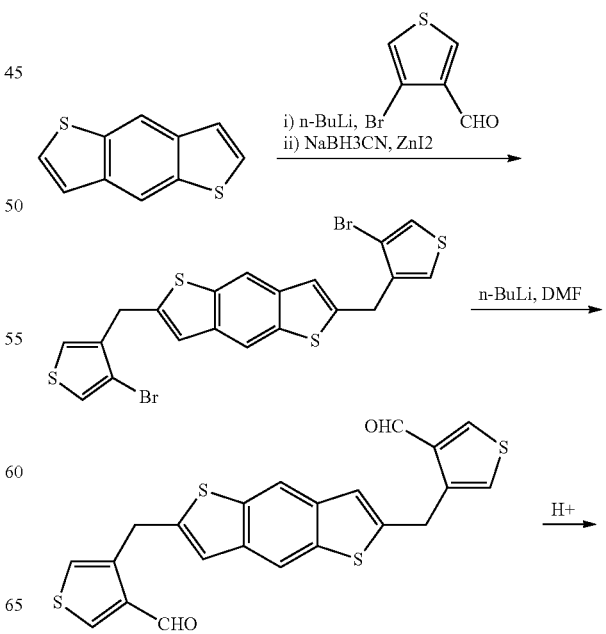

-continued

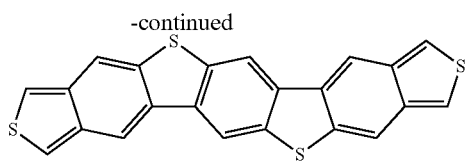

Reaction Schemes 1 and 2 may be performed using a heteroaromatic ring compound substituted with bromine and/or lithium, etc. at about −78° C. to room temperature (about 23° C. to about 25° C.) in an air or nitrogen atmosphere. The solvent may include the commonly used toluene, dimethyl formamide, N-methylpyrrolidinone, tetrahydrofuran, or the like. The catalyst for dehydration in the last step may be an acidic catalyst such as Amberlyst 15 or the like.

A person of ordinary skill in the art may adjust the molecular weight of the fused polycyclic heteroaromatic compound obtained from the synthesis according to one embodiment depending upon the usage and the case, and specifically, the molecular weight is about 350 to about 3000.

According to other example embodiments, an organic thin film including the fused polycyclic heteroaromatic compound and an electronic device including the organic thin film are provided.

The organic thin film according to example embodiments includes the fused polycyclic heteroaromatic compound, so it may be applied to an organic semiconductor layer for an electronic device, or a carrier transport layer such as a channel layer. The electronic device including the same may have excellent electrical properties such as high charge mobility as well as excellent processibility and workability.

The organic thin film may be prepared by dissolving at least one kind of the fused polycyclic heteroaromatic compounds in an organic solvent and depositing the same on a substrate according to the general method, or coating the same at room temperature according to a solution process. If required, heating treatment may be performed after the deposition or coating process to further enhance the densification and uniformity of the thin film.

Particularly, the organic solvent may include at least one kind of general organic solvent, for example, at least one kind of an aliphatic hydrocarbon solvent such as hexane, heptane, or the like; an aromatic hydrocarbon solvent such as toluene, pyridine, quinoline, anisole, mesitylene, xylene, or the like; a ketone-based solvent such as methyl isobutyl ketone, 1-methyl-2-pyrrolidinone, cyclohexanone, acetone, or the like; an ether-based solvent such as tetrahydrofuran, isopropyl ether, or the like; an acetate-based solvent such as ethyl acetate, butyl acetate, propylene glycol methyl ether acetate, or the like; an alcohol-based solvent such as isopropyl alcohol, butanol, or the like; an amide-based solvent such as dimethyl acetamide, dimethyl formamide, or the like; silicone-based solvent; and a mixture of solvents. The amount of the fused polycyclic heteroaromatic compound dissolved in the organic solvent may be adequately selected and determined by a person of ordinary skill in the art, for example, in a range of about 0.01 wt % to about 50 wt % in the total solvent in the view of solubility and coating property.

The method of providing an organic thin film may include thermal deposition, vacuum deposition, laser deposition, screen printing, printing, imprinting, spin casting, dipping, inkjetting, roll coating, flow coating, drop casting, spray coating, roll printing, or the like, but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent by a person of ordinary skill in the art, and is specifically in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, a sensor, or the like, and the organic thin film may be applied to each device according to the general processes commonly known in the art.

For example, the transistor includes a gate electrode disposed on a substrate; a source electrode and a drain electrode facing each other and defining a channel region; an insulation layer electrically insulating the source electrode and drain electrode and the gate electrode; and an active layer including the fused polycyclic heteroaromatic compound formed in the channel region.

The active layer may be obtained by applying a composition including the fused polycyclic heteroaromatic compound to a solution process such as screen printing, printing, spin coating, dipping, ink jetting, or the like. When the active layer is formed by the solution process, the process cost may be reduced, and a wide area device may be effectively fabricated.

Figure 2:
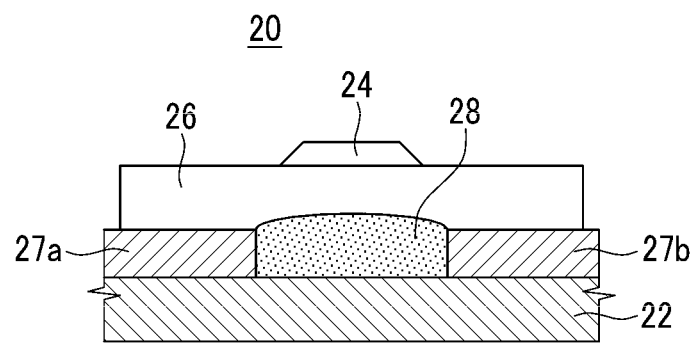

FIGS. 1 and 2 are schematic cross-sectional views showing a transistor according to example embodiments.

The transistor according to example embodiments may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. On the insulation layer 16, a source electrode 17a and a drain electrode 17b defining a channel region are provided, and an active layer 18 is provided in the channel region. The active layer 18 includes the fused polycyclic heteroaromatic compound.

Referring to FIG. 2, a transistor 20 includes a source electrode 27a and a drain electrode 27b defining a channel region and that are formed on a substrate 22, and an active layer 28 formed on the channel region. The active layer 28 includes the fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic such as polyethylene naphthalate (PEN), polyethylene terephthalate (PET), polycarbonate, polyvinyl alcohol, polyacrylate, polyimide, polynorbornene, polyethersulfone (PES) and combinations thereof, and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), indium tin oxide (ITO) or combinations thereof, but it is not limited thereto.

The insulation layers 16 and 26 may include: a generally-used insulator having a high dielectric constant, particularly a ferroelectric insulator such as $Ba_{0.33}Sr_{0.66}TiO_3$ (BST, barium strontium titanate), $Al_2O_3$, $Ta_2O_5$, $La_2O_5$, $Y_2O_3$, and $TiO_2$; an inorganic insulator such as $PbZr_{0.33}Ti_{0.66}O_3$ (PZT), $Bi^4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_x$, AlON, and so on; or an organic insulator such as polyimide, benzocyclobutane (BCB), parylene, polyacrylate, polyvinyl alcohol, polyvinylphenol, and the like, without limitation. Although it is not mentioned above, the inorganic insulator disclosed in U.S. Pat. No. 5,946,551 and the organic insulator disclosed in U.S. Pat. No. 6,232,157 may be used for the insulation layers 16 and 26.

The foregoing is illustrative of example embodiments and is not to be construed as limiting thereof. Although a few example embodiments have been described, those skilled in the art will readily appreciate that many modifications are possible in example embodiments without materially departing from the novel teachings. Accordingly, all such modifications are intended to be included within the scope of the disclosure as defined in the claims. Therefore, it is to be understood that the foregoing is illustrative of various example embodiments and is not to be construed as limited to the specific embodiments disclosed, and that modifications to the disclosed embodiments, as well as other embodiments, are intended to be included within the scope of the appended claims.

What is claimed is:

1. A fused polycyclic heteroaromatic compound represented by the following Chemical Formula 1:

[Chemical Formula 1]

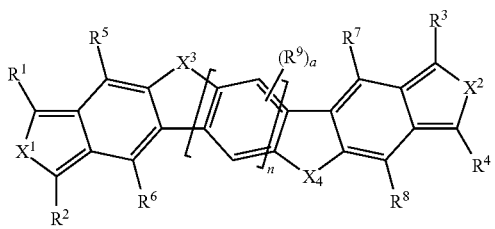

wherein, in Chemical Formula 1,
$X^1$ and $X^2$ are each independently O, S, Se, Te or N—$R^a$, wherein $R^a$ is hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group (—$OR^{11}$, wherein $R^{11}$ is a substituted or unsubstituted C6 to C30 aryl group), a substituted or unsubstituted C4 to C30 cycloalkyl group, a substituted or unsubstituted C4 to C30 cycloalkyloxy group (—$OR^{12}$, wherein $R^{12}$ is a substituted or unsubstituted C4 to C30 cycloalkyl group), a substituted or unsubstituted C2 to C30 heteroaryl group, an acyl group (—C(=O)$R^{13}$, wherein $R^{13}$ is a substituted or unsubstituted C1 to C30 alkyl group), a sulfonyl group (—S(=O)$R^{14}$, wherein $R^{14}$ is a substituted or unsubstituted C1 to C30 alkyl group), or a carbamate group (—$NH_2C$(=O)$OR^{15}$, wherein $R^{15}$ is a substituted or unsubstituted C1 to C30 alkyl group),
$X^3$ and $X^4$ are each independently O, S, Se, Te, N—$R^b$ or $CR^cR^d$ wherein $R^b$ to $R^d$ are each independently hydrogen, a substituted or unsubstituted linear or branched C1 to C30 alkyl group, a substituted or unsubstituted C7 to C30 arylalkyl group, a substituted or unsubstituted C6 to C30 aryl group, a substituted or unsubstituted C1 to C30 alkoxy group, a substituted or unsubstituted C6 to C30 aryloxy group (—$OR^{11}$, wherein $R^{11}$ is a substituted or unsubstituted C6 to C30 aryl group), a substituted or unsubstituted C4 to C30 cycloalkyl group, a substituted or unsubstituted C4 to C30 cycloalkyloxy group (—$OR^{12}$, wherein $R^{12}$ is a substituted or unsubstituted C4 to C30 cycloalkyl group), a substituted or unsubstituted C2 to C30 heteroaryl group, an acyl group (—C(=O)$R^{13}$, wherein $R^{13}$ is a substituted or unsubstituted C1 to C30 alkyl group), a sulfonyl group (—S(=O)$R^{14}$, wherein $R^{14}$ is a substituted or unsubstituted C1 to C30 alkyl group), or a carbamate group (—$NH_2C$(=O)$OR^{15}$, wherein $R^{15}$ is a substituted or unsubstituted C1 to C30 alkyl group),
$R^1$, $R^2$, $R^3$, $R^4$, $R^5$, $R^6$, $R^7$, $R^8$, and $R^9$ are each independently hydrogen, halogen(—F, —Cl, —Br or —I), a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group,
n is an integer ranging from 0 to 3, and
a is an integer of 1 or 2.

2. The fused polycyclic heteroaromatic compound of claim 1, wherein the fused polycyclic heteroaromatic compound is represented by the following Chemical Formula 1A:

[Chemical Formula 1A]

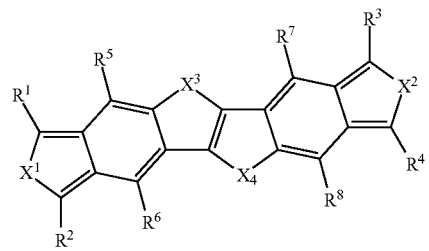

wherein, in Chemical Formula 1A,
$X^1$, $X^2$, $X^3$, $X^4$, $R^1$, $R^2$, $R^3$, $R^4$, $R^5$, $R^6$, $R^7$, and $R^8$ are each independently the same as in Chemical Formula 1.

3. The fused polycyclic heteroaromatic compound of claim 1, wherein the fused polycyclic heteroaromatic compound is represented by the following Chemical Formula 1B:

[Chemical Formula 1B]

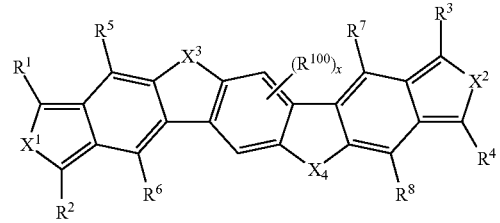

Wherein, in Chemical Formula 1B,
$X^1$, $X^2$, $X^3$, $X^4$, $R^1$, $R^2$, $R^3$, $R^4$, $R^5$, $R^6$, $R^7$, and $R^8$ are the same as in Chemical Formula 1,
$R^{100}$ is the same as $R^9$ of Chemical Formula 1, and
x is an integer of 1 or 2.

4. The fused polycyclic heteroaromatic compound of claim 1, wherein the fused polycyclic heteroaromatic compound is represented by the following Chemical Formulae 1C to 1E:

[Chemical Formula 1C]

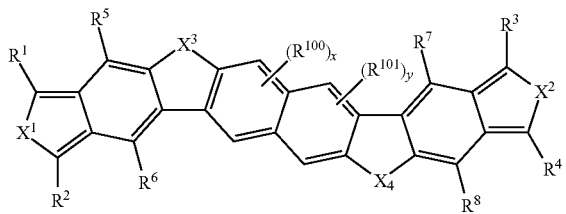

[Chemical Formula 1D]

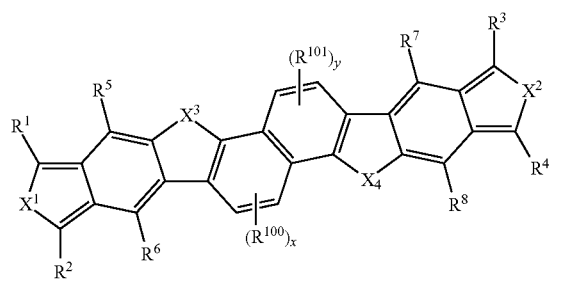

[Chemical Formula 1E]

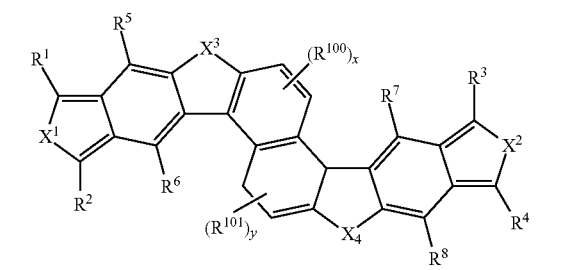

Wherein, in Chemical Formulae 1C to 1E, $X^1$, $X^2$, $X^3$, $X^4$, $R^1$, $R^2$, $R^3$, $R^4$, $R^5$, $R^6$, $R^7$, and $R^8$ are the same as in Chemical Formula 1, $R^{100}$ and $R^{101}$ are each independently the same as $R^9$ of Chemical Formula 1, and x and y is an integer of 1 or 2.

5. The fused polycyclic heteroaromatic compound of claim 1, wherein the fused polycyclic heteroaromatic compound is represented by the following Chemical Formulae 1F to 1H:

[Chemical Formula 1F]

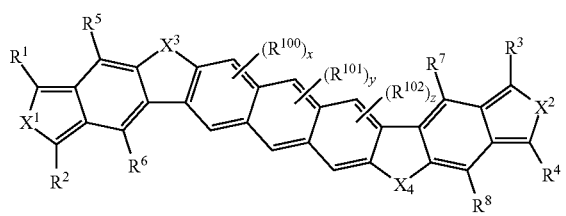

[Chemical Formula 1G]

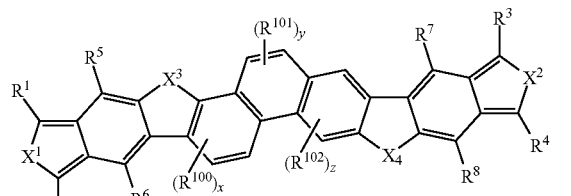

[Chemical Formula 1H]

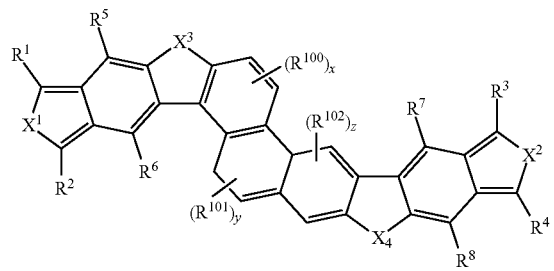

Wherein, in Chemical Formulae 1F to 1H, $X^1$, $X^2$, $X^3$, $X^4$, $R^1$, $R^2$, $R^3$, $R^4$, $R^5$, $R^6$, $R^7$, and $R^8$ are the same as in Chemical Formula 1, $R^{100}$ to $R^{102}$ are each independently the same as $R^9$ of Chemical Formula 1, and x, y and z is an integer of 1 or 2.

6. The fused polycyclic heteroaromatic compound of claim 1, wherein, in Chemical Formula 1, $X^1$, $X^2$, $X^3$, and $X^4$ are sulfur (S).

7. The fused polycyclic heteroaromatic compound of claim 1, wherein the fused polycyclic heteroaromatic compound has an average molecular weight of about 350 to about 3000.

8. The fused polycyclic heteroaromatic compound of claim 1, wherein n is an integer ranging from 1 to 3.

9. The fused polycyclic heteroaromatic compound of claim 1, wherein, in Chemical Formula 1, at least one of $X^1$, $X^2$, $X^3$, and $X^4$ is sulfur (S).

10. The fused polycyclic heteroaromatic compound of claim 1, wherein, in Chemical Formula 1, at least one of $R^1$, $R^2$, $R^3$, $R^4$, $R^5$, $R^6$, $R^7$, $R^8$, and $R^9$ is independently a substituted or unsubstituted linear or branched C1 to C30 alkyl group, a substituted or unsubstituted linear or branched C2 to C30 alkenyl group, a substituted or unsubstituted linear or branched C2 to C30 alkynyl group, a substituted or unsubstituted C7 to C30 arylalkyl group, a substituted or unsubstituted C2 to C30 heteroarylalkyl group, a substituted or unsubstituted C2 to C30 alkylheteroaryl group, a substituted or unsubstituted C5 to C30 cycloalkyl group, a substituted or unsubstituted C2 to C30 heterocycloalkyl group, a substituted or unsubstituted C6 to C30 aryl group, or a substituted or unsubstituted C2 to C30 heteroaryl group.

11. An organic thin film, comprising:
the fused polycyclic heteroaromatic compound according to claim 1.

12. An electronic device, comprising:
the fused polycyclic heteroaromatic compound according to claim 1.

13. The electronic device of claim 12, wherein the electronic device is one selected from a transistor, an organic light emitting diode (OLED), a photovoltaic device, a solar cell, a laser device, a memory, and a sensor.

14. The electronic device of claim 12, further comprising:
a transistor including an active layer formed of the fused polycyclic heteroaromatic compound in a channel region.

* * * * *